United States Patent [19]

Heimberger

[11] Patent Number: 5,443,422
[45] Date of Patent: Aug. 22, 1995

[54] SHAFT FOR FLEXIBLE TECHNICAL AND SURGICAL ENDOSCOPES

[75] Inventor: Rudolf Heimberger, Oberderdingen, Germany

[73] Assignee: Richard Wolf GmbH, Knittlingen, Germany

[21] Appl. No.: 58,115

[22] Filed: May 5, 1993

[30] Foreign Application Priority Data

Mar. 12, 1993 [DE] Germany .................. 93 03 603.5

[51] Int. Cl.[6] .................. A61B 1/00; G02B 23/24
[52] U.S. Cl. .................... 464/57; 464/183; 138/127; 87/9
[58] Field of Search ............ 464/160, 183; 87/6, 87/7, 8, 9; 128/4; 138/125, 127, 133

[56] References Cited

U.S. PATENT DOCUMENTS

| 656,187 | 8/1900 | Gunnell | 138/127 X |
|---|---|---|---|
| 840,066 | 1/1907 | Jones | 87/9 X |
| 2,367,944 | 1/1945 | Ingalls | 138/133 X |
| 2,962,050 | 11/1960 | Ramberg et al. | 138/127 X |
| 4,200,126 | 4/1980 | Fish | 138/127 |
| 4,802,510 | 2/1989 | Berlincourt et al. | 138/125 |
| 4,817,613 | 4/1989 | Jaraczewski et al. | 87/8 X |
| 4,860,631 | 8/1989 | Aoshiro | 87/9 |

FOREIGN PATENT DOCUMENTS 2006406 8/1970 Germany .

OTHER PUBLICATIONS

Brochure of Richard Wolf GmbH, "Technoscope 20" (VI.92), 2 pages (Jun. 1, 1992).
Brochure of Olympus Industrial, "Fiberscopes—O-ESIF8D4X1-20 Fiberscope for CCTV", 1 page, undated.
Brochure of Machida, Inc., "Why You Need the Best Borescope Available", 1 page, undated.

Primary Examiner—Clifford D. Crowder
Assistant Examiner—John J. Calvert
Attorney, Agent, or Firm—Panitch Schwarze Jacobs & Nadel

[57] ABSTRACT

The flexible shaft suitable for technical and surgical endoscopes consists at least partly of circular braiding of webs interwoven with one another. A particularly stable and torsion-resistant shaft also having low wall thickness is produced in that weaving of the webs formed by the flat wires is single-braided, and in that the circular braiding is machined by hammering, particularly in the region of the crisscrosses of the flat wires.

1 Claim, 4 Drawing Sheets

SHAFT FOR FLEXIBLE TECHNICAL AND SURGICAL ENDOSCOPES

BACKGROUND OF THE INVENTION

1. Field of the Invention

The invention relates to a shaft for flexible technical and surgical endoscopes which at least partly comprises circular braiding of webs interwoven with one another.

2. Description of the Prior Art

In known shafts of this type, the webs or layers of the braiding consist of circular wires which run parallel or are interwoven to form braidings. The braiding machine must be fitted with a number of wire coils corresponding to the number of wires, with corresponding complexity, because of the plurality of wires required for constructing such circular braiding. In addition, in the conventional method of braiding using circular wires, it is not possible to achieve a low wall thickness, since even for a parallel arrangement of the wires belonging to a web, the bending radii thereof are relatively large in the region of the crisscrosses. This disadvantage can also be detected particularly in circular braidings, the webs of which are braidings or flat braidings.

Finally, braidings produced from circular wires are unstable and have low torsion resistance. This applies particularly also if braiding of the webs is additionally carried out to be double-braided or polybraided, hence for example the braiding is '2 over 2', in which one web after the other in each case runs initially over two and then below two webs crossing them. When using braidings of this type for endoscope shafts, mechanical stabilisation is therefore usually required which consists of a flat wire helix lying on the inside in most cases and supporting the braiding from the inside.

The object of the invention consists in providing an endoscope shaft having a circular braiding which is simple to manufacture and which is dimensionally stable and torsion resistant in spite of low wall thickness, but otherwise has adequate flexibility.

SUMMARY OF THE INVENTION

To achieve this object, the invention provides a shaft for flexible technical and surgical endoscopes, which at least partly comprises circular braiding of webs interwoven with one another, wherein braiding of the webs formed by flat wires is single-braided.

On the one hand, the use of flat wires as braided webs allows low manufacturing effort because of the comparatively small number of wire coils required at the braiding machine. On the other hand, the flat wires may be thinner compared to the diameter of the circular wires otherwise used for known shaft braidings and nevertheless have adequate mechanical strength. Hence, it is thus possible to keep the wall thickness of the shaft low.

The single-braided weaving produces twice the number of crossing points compared to braiding practised hitherto and for example double-braided weaving, and this leads to a considerable increase in the stability and torsional strength, particularly since the webs are as it were intermeshed it the crisscrosses with other opposed webs, it being possible for these positive joints of the almost meandering webs to be strengthened further by machining the circular braiding by hammering or pressing, particularly in the region of the flat wire crisscrosses.

At the same time, such a machining step ensures that the wall thickness of the braiding is essentially only twice the thickness of a flat wire and that the braiding has a smooth surface which is resistant to wear. Moreover, the shaft is sufficiently stable during bending processes in spite of low wall thickness, so that internal supports may be dispensed with, particularly for small shaft diameters.

Furthermore, metal flat wire braiding also offers the advantage that it may be soldered as well as bonded in contrast to a braiding made from metal circular wires, which may only be strengthened by soldering and may be joined to other parts. Hence, for example the ends of the circular braiding can be bonded by means of laser irradiation to produce rigid tubular shaft ends if required.

Finally, the circular braiding alone may form an endoscope shaft. However, it may also only form a section or part of the shaft, for example its outer sleeve, or may be covered with an external tube.

BRIEF DESCRIPTION OF THE DRAWINGS

The foregoing summary of the invention, as well as the following detailed description of the preferred embodiments, will be better understood when read in conjunction with the appended drawings. For the purposes of illustrating the invention, there are shown in the drawings embodiments which are presently preferred, it being understood, however, that the invention is not limited to the specific arrangements and instrumentalities disclosed. In the drawings.

DESCRIPTION OF THE PREFERRED EMBODIMENTS

Figure 1:
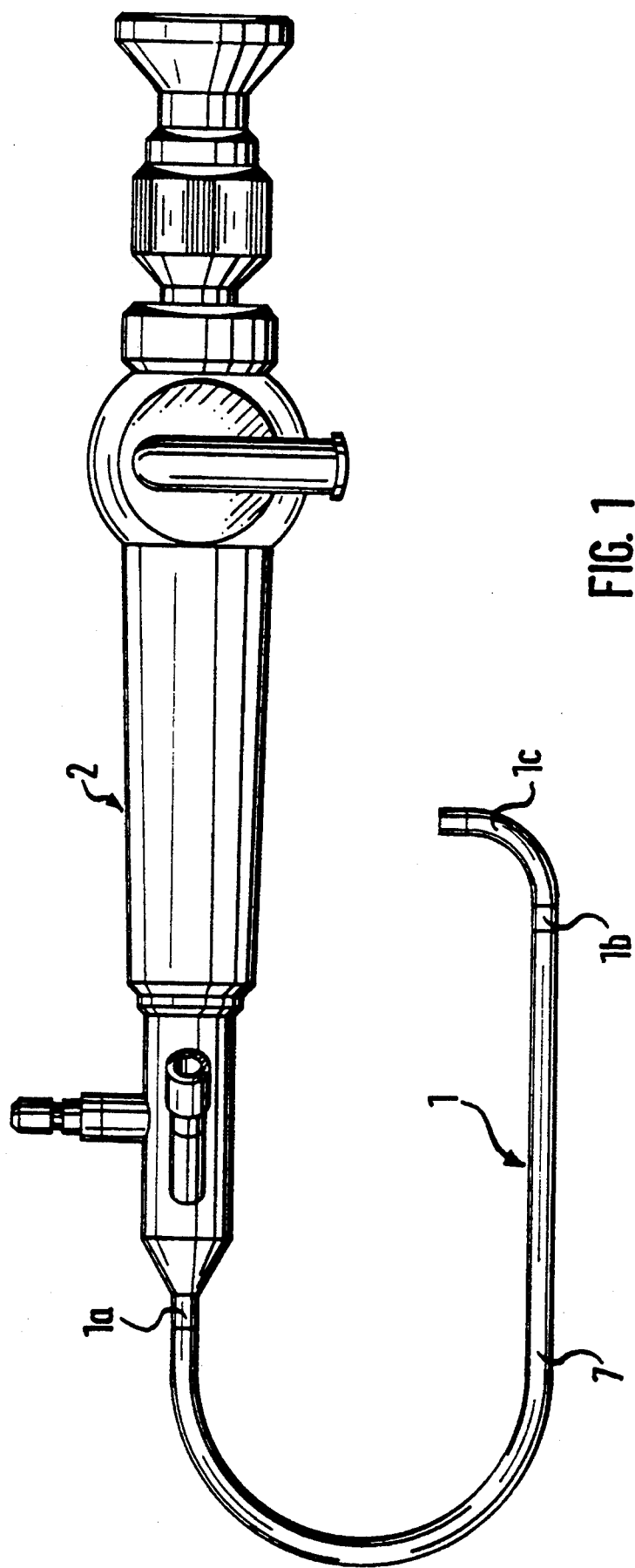
FIG. 1 shows an endoscope having a shaft constructed in accordance with the invention.

Referring to FIG. 1, the endoscope therein has a flexible shaft 1, which is attached proximally to a rigid endoscope part 2, it being possible to stabilise the flat wire braiding, described in further detail later, there by means of bonding, so that a shaft section 1a is provided in the form of a rigid tube which is joined to the distal end of the endoscope part 2. The shaft section 1b may also be designed in corresponding manner in the region where the shaft 1 merges into its steerable distal end 1c.

Figure 2:
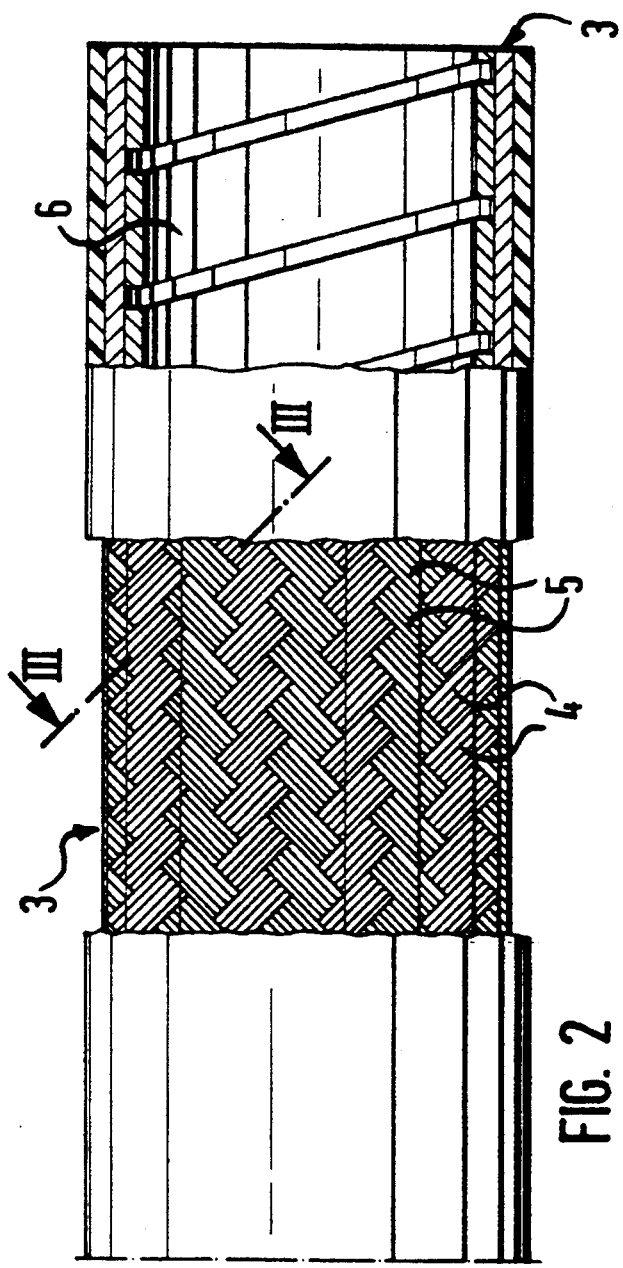
FIG. 2 shows a shaft section having a circular braiding of known type.
Figure 3:
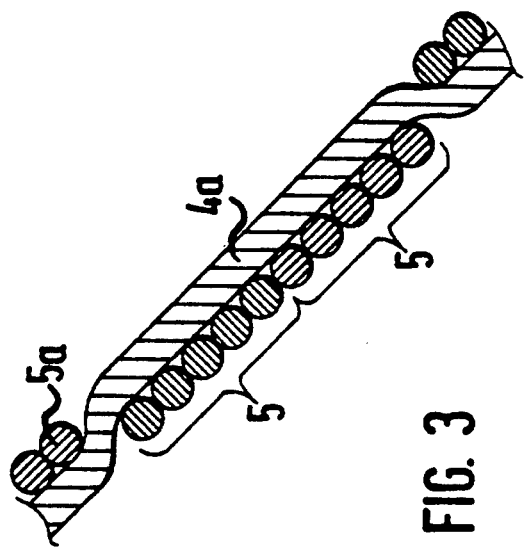
FIG. 3 shows a section along the sectional line III—III in FIG. 2.

FIG. 2 shows a conventional design of a circular braiding 3, the crossing webs 4, 5 of which consist, for example of five parallel circular wires 4a, 5b, the weaving of the webs being double-braided, that is that braiding weaving is '2 over 2'. Circular braidings of this type must be supported because of the disadvantages described in the introduction, and particularly because of the low stability. This is generally supplied by means of an inner helix 6 made from metal ribbon.

Figure 4:
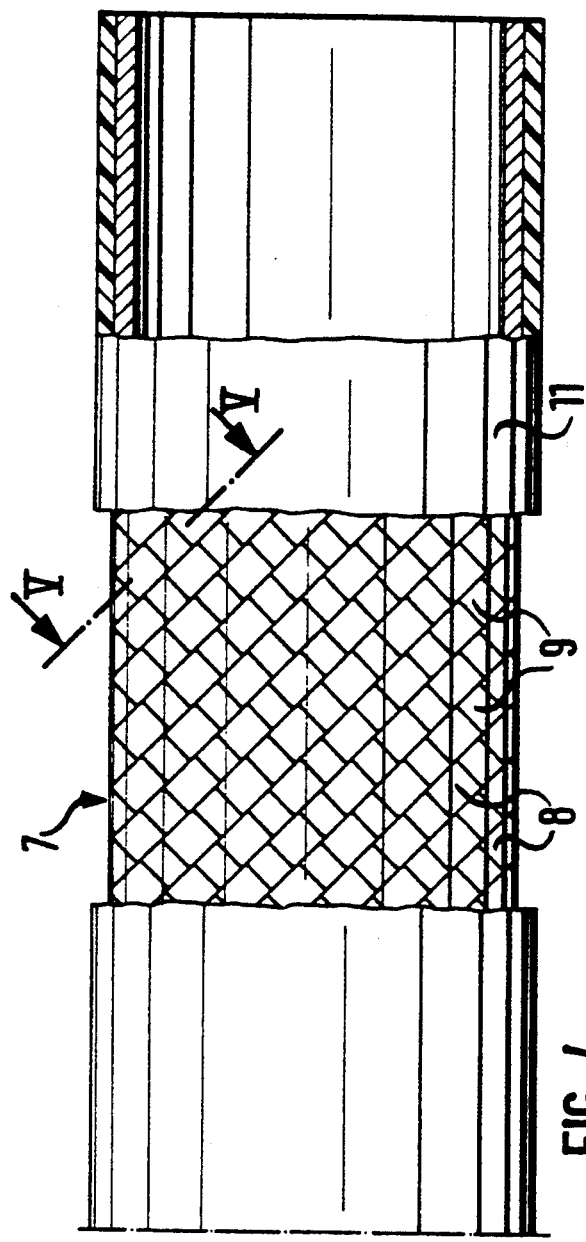
FIG. 4 shows a shaft section having a flat wire braiding.
Figure 5:
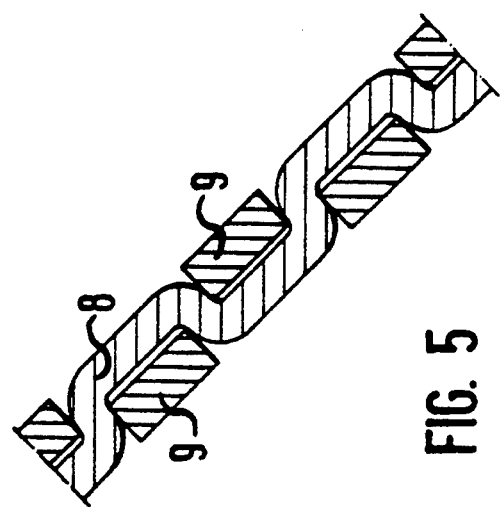
FIG. 5 shows a section taken along the sectional line V—V in FIG. 4.
Figure 6:
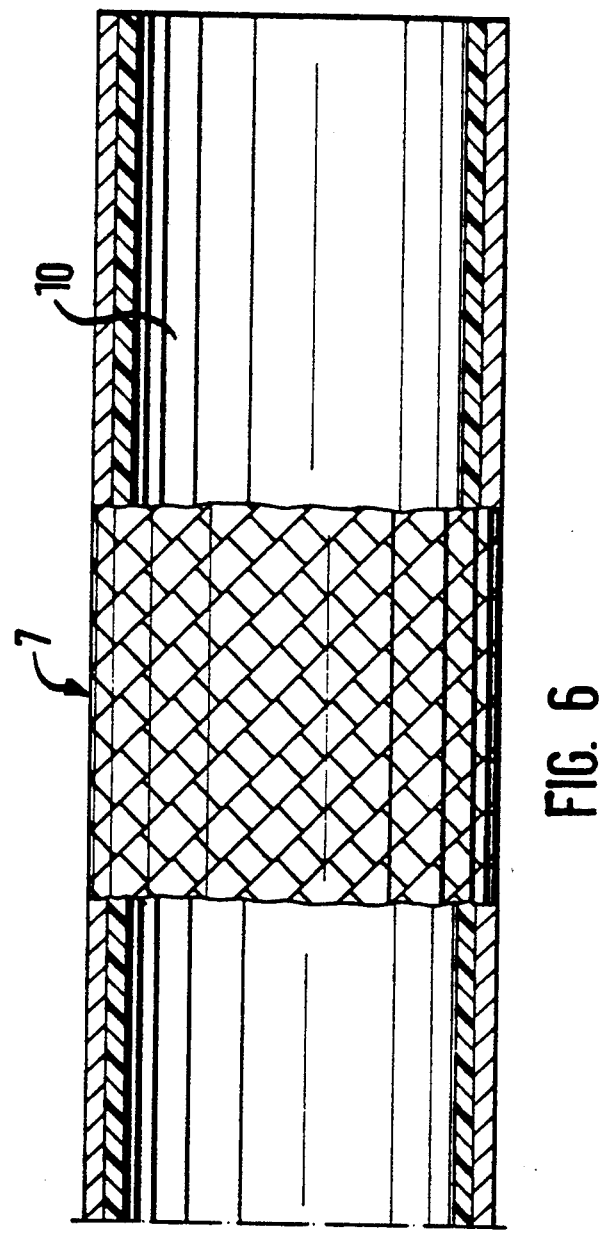
FIG. 6 shows a partially longitudinally sectioned shaft section having a flat wire braiding.

For the circular braiding 7 shown in FIGS. 4 and 6, the webs according to the invention consist of flat wires 8, 9, which are interwoven '1 over 1', so that their weaving is single-braided.

As already mentioned, this circular braiding per se may form an endoscope shaft having low wall thickness. However, it may also be used as only part of a shaft, more specifically, for example according to FIG. 6, as a sheath for a tube 10. On the other hand, the tubular braiding corresponding to FIG. 4 may also form an inner part of the shaft and be covered by an external tube 11.

A fluid-tight design for the shaft is achieved by means of the tubes 10, 11. Moreover, the tubes may also assume the function of a support for the tubular braiding, but this will usually only be necessary for shafts or tubular braidings having relatively large diameter.

The present invention may be embodied in other specific forms without departing from the spirit or essential attributes thereof and, accordingly, reference should be made to the appended claims rather than to the foregoing specification as indicating the scope of the invention.

I claim:

1. A shaft for flexible technical and surgical endoscopes, said shaft comprising at least in part a circular braiding of webs interwoven with each other, said webs comprising flat wires and said braiding being single-braided, the flat wires having regions of crisscrosses with each other, the circular braiding being machined by hammering in the regions of the crisscrosses, and the flat wires being bonded together adjacent to at least one end of the circular braiding to form a rigid tube at the end.

* * * * *